United States Patent

Pirani

[11] Patent Number: 6,061,127
[45] Date of Patent: May 9, 2000

[54] DEVICE FOR REGISTERING PARAMETERS OF AN ELONGATED TEST MATERIAL

[75] Inventor: Peter Pirani, Grüt/Gossau, Switzerland

[73] Assignee: Zellweger Luwa AG, Switzerland

[21] Appl. No.: 09/095,716

[22] Filed: Jun. 11, 1998

[30] Foreign Application Priority Data

Jun. 11, 1997 [CH] Switzerland .......................... 1410/97

[51] Int. Cl.⁷ .......................... G01N 21/00; G01B 11/00
[52] U.S. Cl. .................. 356/238.2; 356/381; 356/387; 356/429; 356/372
[58] Field of Search .......................... 356/238.2, 237.1, 356/372, 381, 386, 387, 429

[56] References Cited

U.S. PATENT DOCUMENTS

| | | | |
|---|---|---|---|
| 5,054,317 | 10/1991 | Laubscher | 73/160 |
| 5,114,230 | 5/1992 | Pryor | 356/372 |
| 5,167,150 | 12/1992 | Shofner et al. | 356/387 |
| 5,313,692 | 5/1994 | Mizuuchi et al. | 356/430 |
| 5,371,584 | 12/1994 | Scheinhütte | 356/238 |
| 5,414,520 | 5/1995 | Joss et al. | 356/430 |
| 5,696,589 | 12/1997 | Bernacki | 356/381 |

FOREIGN PATENT DOCUMENTS

| | | |
|---|---|---|
| 0 401 600 | 1/1996 | European Pat. Off. . |
| 195 18 785 | 11/1999 | Germany . |

OTHER PUBLICATIONS

Müller, Jörg R., "Fremdfasern in Der Spinnerei", Melliand Textilberichte, International Textile Reports, vol. 76, No. 3, Mar. 1, 1995, pp. 124–125, 128.

*Primary Examiner*—Frank G. Font
*Assistant Examiner*—Roy M. Punnoose
*Attorney, Agent, or Firm*—Burns, Doane, Swecker & Mathis

[57] ABSTRACT

A device for registering parameters of an elongated test material that takes up little space, can be manufactured easily and is cost-effective includes a light source for illuminating at least one region of the test material. The light source is in the form of a radiator of planar construction which is preferably designed for the emission of diffuse light. The radiator is connected to an electrode that is transparent and that can be applied to the radiator in the form of a layer.

14 Claims, 2 Drawing Sheets

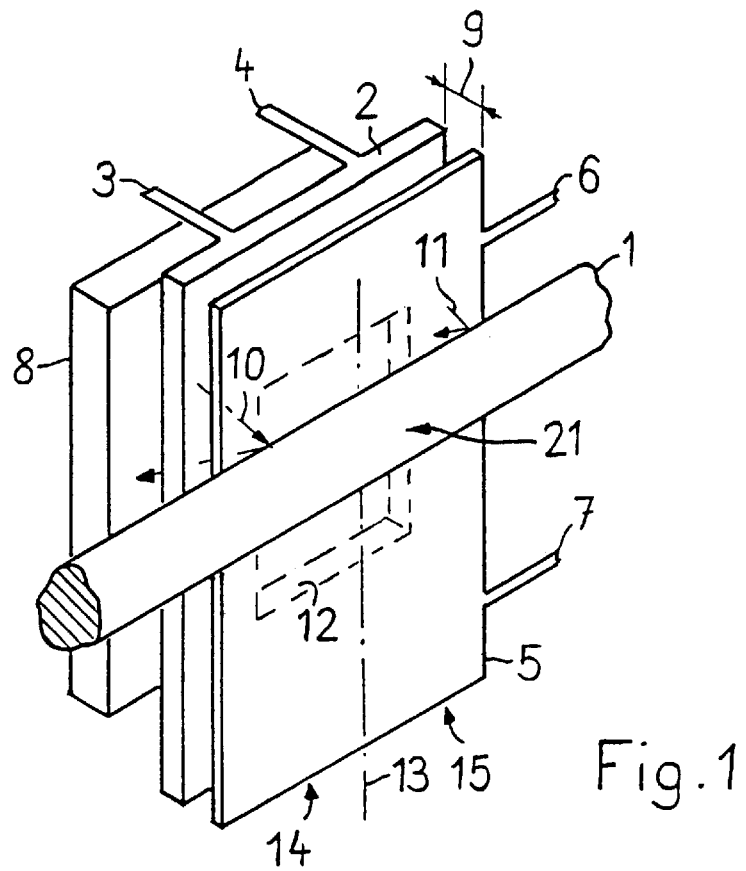
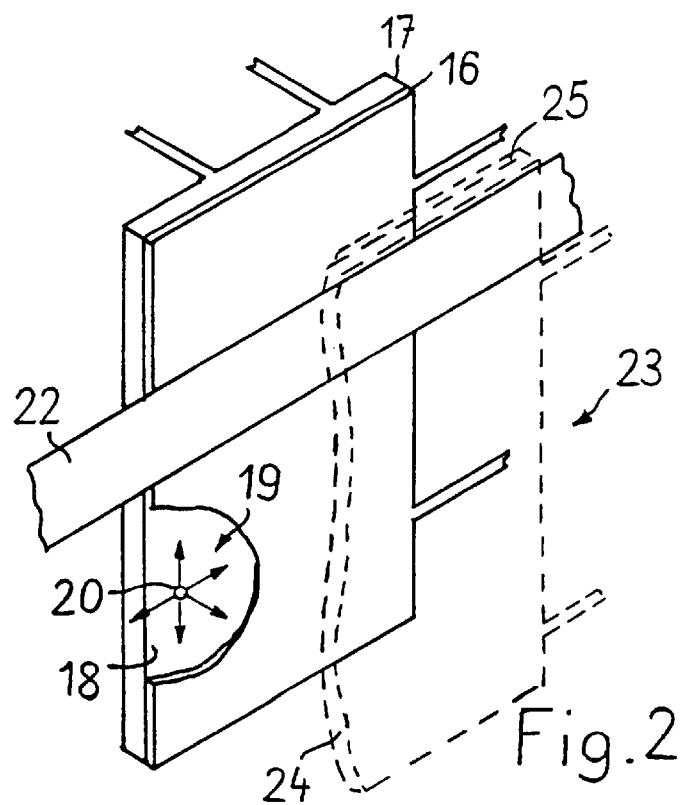

DEVICE FOR REGISTERING PARAMETERS OF AN ELONGATED TEST MATERIAL

FIELD OF THE INVENTION

The invention relates to a device for registering parameters of an elongated test material, said device comprising elements for generating a beam path in a region of the test material.

BACKGROUND OF THE INVENTION

From EP 0 401 600 such a device is already known for a test material in thread or wire form, wherein provision is made for a measuring gap, on each of the side walls of which a measuring electrode forming part of a capacitive measuring element is provided. In addition to the capacitive measuring element an optical measuring element is provided, comprising a light source arranged on one side of the measuring gap and a photoelectric element arranged on the other side of the measuring gap. With a view to generating a homogeneous field of illumination in the measuring gap, an aperture or a light guide in the form of a truncated cone is provided between the light source and the measuring gap.

A disadvantage of this known device can be seen in the fact that, in addition to the measuring gap, a lot of space is taken up for the light source and for means for guiding the beam of light. In addition, these means and the light source may have to be separably attached to one another or to a support stand, resulting overall in a solution that saves little space and is not very cost-effective.

SUMMARY OF THE INVENTION

The invention as described below now achieves the object of creating a device of the stated type that takes up little space, can be manufactured easily and is inexpensive.

This is achieved by at least one of the elements that generate a beam path in the region of the test material being of planar construction. Such an element may advantageously be a diffuse radiator of planar construction which acts as a light source. In the region of the elements, electrodes should furthermore be provided that are transmitting with respect to the beams pertaining to the beam path, namely transparent in the case of light beams in particular, and that are preferably applied to the element in the form of a layer. Assigned to the element that acts as beam source or light source is an element that acts as detector and receives beams from the radiator, in which connection said beams may be occluded by the test material or reflected on the test material.

The advantages obtained by means of the invention can be seen in particular in the fact that sensors operating optically and capacitively at the same time can be constructed very simply, cheaply and in space-saving manner. Hence the bulk and the cross-section or diameter of the test material, for example, can be registered simultaneously. The low space requirement allows further sensors that register various properties in respect of a test material to be provided additionally in a predetermined space. For example, in addition to sensors for registering the irregularity of bulk and diameter of the test material, further sensors for registering extraneous substances or the surface structure of the test material may accordingly be provided. Or the same property may be registered by two or more sensors having different characteristics, for example different spectral sensitivities. If the device according to the invention is constructed for textile yarns, then it may be part of a yarn clearer which has reduced external dimensions and can consequently be easily installed at selected points in a textile machine, something which, as is generally known, is not always possible, since little space is usually available on a textile machine for additional apparatus, or at least not at those places where registration of the yarn is meaningful for monitoring or measurement of the yarn.

BRIEF DESCRIPTION OF THE DRAWING FIGURES

In the following we have elucidated the invention in more detail on the basis of an example and with reference to the enclosed drawings. Illustrated are:

FIGS. 1 and 2: in each case a simplified representation of a device according to the invention with a test material, FIGS. 3 and 4: a part of an element of the device, and FIG. 5: a device with a measuring gap.

DETAILED DESCRIPTION OF THE INVENTION

Figure 3:
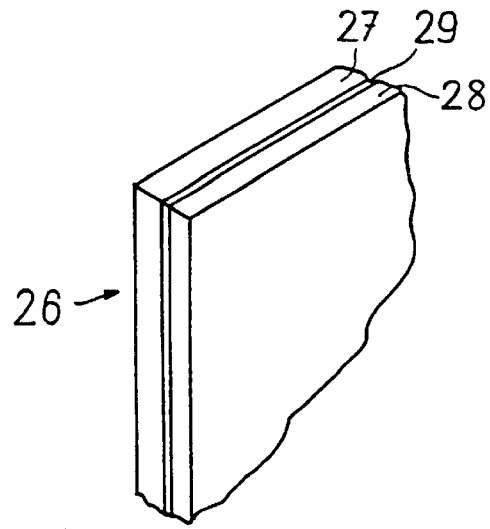

FIG. 1 shows a device according to the invention for a test material 1, said device consisting of an element 2 of planar construction, here a radiator or a beam source, with electrical connectors 3 and 4, an electrode 5 with connectors 6 and 7, and of a further element 8, here likewise of planar construction, a beam sink (usually a detector) with connectors which are not visible here. With this construction the electrode 5 is arranged at a distance 9 from the radiator 2, and both register a region 21 of the test material 1.

The electrode 5 is transmitting with respect to the radiation of the element 2, so that a beam path 10, 11 between the elements 2, 8 that emanates from the radiator 2 and is reflected on the test material 1 falls back onto the radiator 2 and, if the radiator 2 is also transmitting, is able to pass through the radiator 2 and strike the detector 8, where incoming beams are converted into an electrical signal, for example in a manner known as such. In the case of a non-transmitting radiator 2 the radiation 10, 11 may also pass through the radiator 2 through a window 12 in the latter and strike the detector 8.

However, it is also possible, as will be shown below, to provide on the side of the test material 1 facing away from the radiator 2 a detector which receives the radiation that is not occluded by the test material 1. It is also possible to split the device into two halves which extend to the left and to the right of the dot-dashed line 13, so that each half 14, 15 radiates a radiation with a definite property differing from the radiation in the other half. For example, each half 14, 15 could emit light of a different wavelength. Similarly it would be possible to arrange the electrode 5 behind the element 2 instead of in front of it.

FIG. 2 shows a device wherein an electrode 16 is arranged on the radiant face 18 of a radiator 17. The electrode 16 may preferably take the form of a layer and be attached to the radiant face 18. The radiant face 18 of the radiator 17 preferably radiates its beams diffusely and in directions such as are represented for a surface element 20 by arrows 19. These directions also include all those in between the individual arrows. It will also be discerned that the test material 22 here takes the form of a tape, for example. Assigned to the element with the radiator 16 and located opposite the electrode 17 is an element 23 which takes the form of a detector for receiving beams, in which connection the actual detector for the beams is provided with the reference symbol 24 and is of planar construction and equipped with an electrode 25.

FIG. 3 shows a part of a device wherein an element 26 is built up from several layers 27, 28. In this case an electrode 29 may also take the form of a layer, arranged between the layers 27, 28. This of course assumes that at least one layer is also transparent to beams. It may also be the case that the electrode 29 is one of the layers necessary for forming the beams and hence performs two functions. This structure is equally suitable for beam sources and for beam sinks (detectors).

Figure 4:
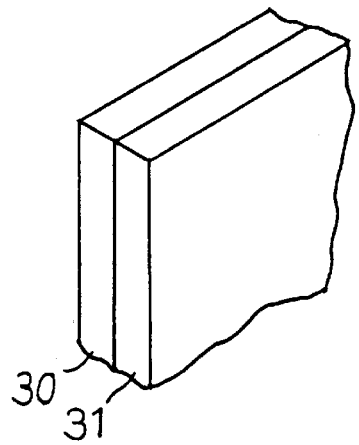

FIG. 4 shows another part of a device wherein several elements are arranged behind or above one another. Here it is possible to discern, for example, two radiators 30 and 31, each of which emits beams having definite properties. Such properties are, for example, different wavelengths of the radiation, different frequencies or modulations etc.

Figure 5:
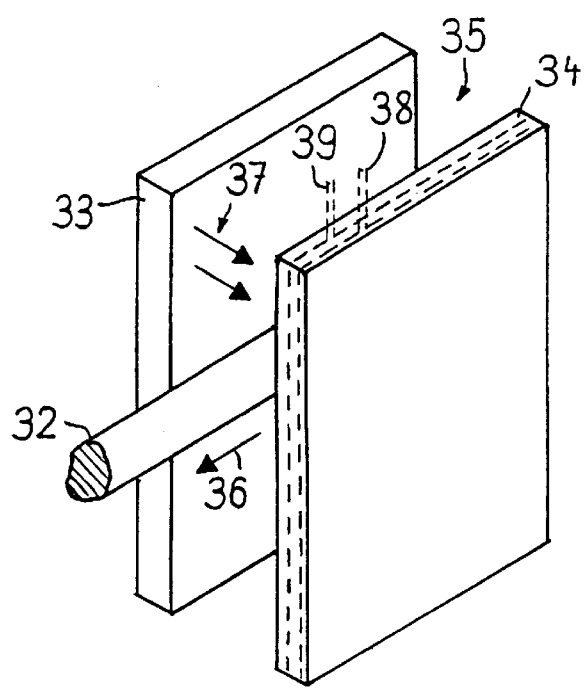

FIG. 5 shows a device for a test material 32 with a beam source 33 and a beam sink 34 which are positioned in relation to one another in such a way that a measuring gap 35 is formed for the test material 32 which is preferably moved in its longitudinal direction, so that a relative movement corresponding to an arrow 36 arises between the device or the measuring gap 35 and the test material 32.

The mode of operation of the device according to the invention is as follows:

With a view to registering parameters in respect of an elongated test material 1 the latter is moved, in a manner known as such and therefore not described here in any detail, past a sensor as represented by elements having reference symbols 2, 5, 8, 17 etc. With this device it is intended to register the bulk, capacitively for example, and, optically, the diameter or cross-section of the test material or alternatively the irregularities thereof over the length. However, instead of, or in addition to, the irregularities it is also possible, in the case of yarn for example, for the hairiness, the extraneous-fibre content etc to be registered. Instead of optical waves, other waves or beams may be employed. Registration may be undertaken for the purpose of a measurement or for the purpose of monitoring. For the subsequent part of the specification it will be supposed that this parameter is to be registered, on the one hand, by means of an electric field and, on the other hand, by means of radiation, here in the form of light beams.

For a first registration the test material 1 is therefore illuminated in its region 21 by light beams from the radiator 2 which may pass largely unattenuated through a transparent electrode 5. The light beams are emitted as diffusely as possible, as is evident from FIG. 2. Said light beams may be registered, in the sense of a measurement of transmitted light, by a receiver or beam sink 34 (FIG. 5). Owing to absorption, reflection and scattering, the receiver 34 then receives only a fraction of the radiation emitted by the radiator 2. From the amount of light received it is accordingly possible for a signal to be derived in known manner which represents the curve of the parameter that is being sought.

For a second registration the same region 21 of the test material 1, 32 can be moved through an electric field 37 (FIG. 5) located between electrodes which are present in the transmitter 33 and receiver 34 and which are constructed as represented in FIGS. 1 to 3. Between the electrodes, which preferably have the same structure in the receiver 34 as in the transmitter 31, the changes in the electric field caused by the test material can be measured in known manner, so that a curve of the parameter that is being sought can also be obtained in this way.

If the electrodes are not of transparent construction, the light beams may pass through a window 12 and accordingly impinge on the test material 1. Reflected light beams may similarly pass through the window 12 and the transmitter to reach the detector 8, whereas transmitted light beams may pass through a corresponding window in the electrode of the receiver 34 to reach a detector where their residual intensity is registered. In the case of strongly diffuse radiation, sufficient radiation is always present that is influenced by the test material and passes through the windows.

If use is made of several colours for a registration of transmitted light and/or incident light, then a corresponding number of detectors may also be employed which are each selective in only one colour. In addition, a colour selection may also be effected by means of taps 38, 39 for electrons at various depths of a single detector.

All the transmitters and receivers represented with layers may in addition comprise a transparent layer affording protection against harmful environmental influences such as moisture, oxygen, abrasion etc.

Particularly well suited as radiators of planar construction are, for example, luminous polymers such as, for instance, those produced by Cambridge Display Technology in Cambridge, UK.

By planar construction we understand, in particular, the construction of an element such that the beam-emitting face has a length or width substantially greater than the depth of the element, said depth extending approximately perpendicular to the stated face. In other words, the beam-generating element is characterised in that it comprises no other optical elements which form, deflect, scatter etc the beams. This results in a space-saving arrangement. The face that emits beams is the same size as the measuring field. Accordingly connectors 3, 4 and 6, 7 (FIG. 1) for supplying electrical energy are also located close to the test material, preferably separated only by the spacing of the test material from the radiant face and by a fraction of the depth of the element.

What is claimed is:

1. Device for registering a parameter of an elongated test material, comprising an element for generating a beam path in a region of the test material, said element for generating a beam path being a radiator of planar construction which is designed for emission of diffuse light.

2. Device according to claim 1, wherein the radiator generates at least two beam paths having different wavelengths.

3. Device according to claim 2, wherein the beam paths are superimposed on one another.

4. Device according to claim 1, including a detector for receiving the said detector being of planar construction and being operatively associated with the element for generating the beam path.

5. Device according to claim 1, wherein the element comprises a transparent protective layer.

6. Device according to claim 1, including a luminous polymer (LEP) provided by way of the radiator.

7. Device according to claim 1, wherein the element is movable relative to the test material.

8. Device for registering a parameter of an elongated test material, comprising a beam source of planar construction for generating a beam path of diffuse light in a region of the test material and a detector for receiving the light generated by the beam source and converting the light into an electrical signal.

9. Device according to claim 8, wherein the detector is of planar construction.

10. Device according to claim 8, including an electrode which permits transmission therethrough of the light, the beam source being positioned between the electrode and the detector.

11. Device according to claim 8, including an electrode which permits transmission therethrough of the light, the electrode being arranged on a face of the beam source which generates the beam path of diffuse light.

12. Device according to claim 8, wherein the beam source includes a plurality of layers.

13. Device according to claim 8, including two beam sources.

14. Device according to claim 8, wherein the beam source and the detector are spaced apart from one another to form a measuring gap between the beam source and the detector.

* * * * *